United States Patent
Bennani et al.

(10) Patent No.: US 6,316,475 B1
(45) Date of Patent: Nov. 13, 2001

(54) AMINOALKOXYBIPHENYLCARBOXAMIDES AS HISTAMINE-3 RECEPTOR LIGANDS AND THEIR THERAPEUTIC APPLICATIONS

(75) Inventors: Youssef L. Bennani, Lake Bluff; Ramin Faghih, Lake Forest, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/715,601

(22) Filed: Nov. 17, 2000

(51) Int. Cl.$^7$ .......................... A01N 43/40; A01N 43/36; C07D 265/30; C07D 401/10
(52) U.S. Cl. .......................... 514/343; 514/423; 544/176; 548/208; 548/523
(58) Field of Search .......................... 544/176; 546/208; 548/535, 518; 514/343, 423

(56) References Cited

U.S. PATENT DOCUMENTS

| | | | |
|---|---|---|---|
| 5,932,543 | * 8/1999 | Burkhardt et al. | 514/11 |
| 6,232,290 | * 5/2000 | Ohki et al. | 514/11 |

FOREIGN PATENT DOCUMENTS

| | | |
|---|---|---|
| 00/06254 | 2/2000 | (WO) . |
| 0978512AI | 2/2000 | (EP) . |

OTHER PUBLICATIONS

K. Onodera et al., Histamine $H_3$ Antagonists as Potential Therapeutics in the CNS, *The Histamine $H_3$ Receptor*, 255–267 (1998).

P. Panula et al., Brain Histamine in Pathophysiological Conditions and Brain Diseases, *The Histamine $H_3$ Receptor*, 243–253 (1998).

E. Roche (editor), *Bioreversible Carriers in Drug Design*, 1–292 (1987).

C. Tedford, Clinical Application of HA $H_3$ Receptor Antagonists in Learning and Memory Disorders, *The Histamine $H_3$ Receptor*, 269–286 (1998).

J. Arrang et al., Auto–Inhibition of Brain Histamine Release Mediated by a Novel Class ($H_3$) of Histamine Receptor, *Nature*, 302:832–837 (1983).

J. Arrang et al., Highly Potent and Selective Ligands for Histamine $H_3$–Receptors, *Nature*, 327:117–123 (1987).

J. Arrang et al., Histamine $H_3$ Receptor Binding Sites in Rat Brain Membrands; Modulations by Guanine Nucleotides and Divalent Cations, *European Journal of Pharmacology—Molecular Pharmacology Section*, 188:219–227 (1990).

Y. Cheng et al., Relationship Between the Inhibition Constant (KI) and the Concentration of Inhibitor Which Causes 50 Per Cent Inhibition ($I_{50}$) of An Enzymatic Reaction, *Biochemical Pharmacology*, 22: 3099–3108 (1973).

M. De Almeida et al., Memory Facilitation by Histamine, *Arch. Int. Pharmacodyn.*, 283:193–198 (1986).

V. Delaunois et al., Modulation of Acetylcholine, Capsaicin and Substance P Effects by Histamine $H_3$ Receptors in Isolated Perfused Rabbitt Lungs, *European Journal of Pharmacology*, 277:243–250 (1995).

V. Dimitriadou et al., Functional Relationship Between Mast Cells and C–Sensitive Nerve Fibres Evidenced by Histamine $H_3$–Receptor Modulation in Rat Lung and Spleen, *Clinical Science*, 87:151–163 (1994).

V. Dumery et al., Development of Amygdaloid Cholinergic Mediation of Passive Avoidance Learning in the Rat, *Exp. Brain. Res.*, 67:61–69 (1987).

C. Fitzsimons et al., Histamine Receptors Signalling in Epidermal Tumor Cells Lines with H–ras Gene Alterations, *Inflamm. Res.*, 47, Supplement 1, S50–S51 (1998).

H. Haas et al., Subcortical Modulation of Synaptic Plasticity in the Hippocampus, *Behavioural Brain Research*, 66:41–44 (1995).

E. Hatta et al., Activation of Histamine $H_3$ Receptors Inhibits Carrier–mediated Norepinephrine Release in a Human Model of Protracted Myocardial Ishemia[1,2], *The Journal of Pharmacology and Experimental Therapeutics*, 283(2):494–500 (1997).

M. Imamura et al., Activation of Histamine $H_3$–Receptors Inhibits Carrier–Mediated Norepinephrine Release During Protracted Myocardial Ischemia, *Circulation Research*, 78(3):475–481 (1996).

M. Imamura et al., Histamine $H_3$–Receptor–Mediated Inhibition of Calcitonin Gene–Related Peptide Release from Cardiac C. Fibers, *Circulation Research*, 78(5):863–869 (1996).

C. Kamei et al., Influence of Certain $H_1$–Blockers on the Step–Through Active Avoidance Response in Rats, *Psychopharmacology*, 102:312–318 (1990).

C. Kamei et al., Participation of Histamine in the Step–Through Active Avoidance Response and Its Inhibition by $H_1$–Blockers, *Japan J. Pharmacol.*, 57:473–482 (1991).

R. Leurs et al., Histamine Homologues Discriminating between Two Functional $H_3$ Receptor Assays. Evidence for $H_3$ Receptor Heterogeneity?[1], *The Journal of Pharmacology and Experimental Therapeutics*, 276(3):1009–1015 (1996).

(List continued on next page.)

*Primary Examiner*—Floyd D. Higel
*Assistant Examiner*—Kamal Saeed

(57) ABSTRACT

Compounds of formula (I)

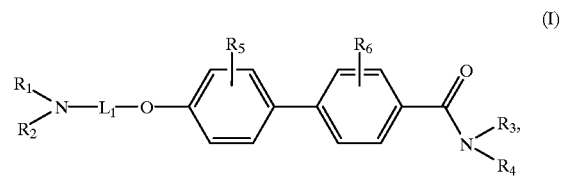

are useful in treating diseases or conditions prevented by or ameliorated with histamine-3 receptor ligands.

22 Claims, No Drawings

OTHER PUBLICATIONS

R. Leurs et al., The Histamine $H_3$–Receptor: A Target for Developing New Drugs, *Progress in Drug Research*, 39:127–165 (1992).

R. Leurs et al., The Medicinal Chemistry and Therapeutic Potentials of Ligands of the Histamine $H_3$ Receptor, *Progress in Drug Research*, 45:107–165 (1995).

R. Leurs et al., Therapeutic Potential of Histamine $H_3$ Receptor Agonists and Antagonists, *Trends in Pharm. Sci*, 19:177–183 (1998).

R. Levi et al., Histamine $H_3$–Receptors: A New Frontier in Myocardial Ischemia, *The Journal of Pharmacology and Experimental Therapeutics*, 292(3):825–830 (2000).

J. Lin et al., Involvement of Histaminergic Neurons in Arousal Mechanisms Demonstrated with $H_3$–Receptor Ligands in the Cat, *Brain Research*, 523:325–330 (1990).

T. Matsubara et al., UK–14,304 R(–) α–Methyl–Histamine and SMS 201–995 Block Plasma Protein Leakage Within Dura Mater by Prejuncitional Mechanisms, *European Journal of Phatmacology*, 224:145–150 (1992).

I. Mazurkiewicz–Kwilecki et al., Changes in the Regional Brain Histamine and Histidine Levels in Postmortem Brains of Alzheimer Patients, *Can. J. Physiol. Pharmacol*, 67: 75–78 (1989).

J. Monti et al., Effects of Selective Activation or Blockade of the Histamine $H_3$ Receptor on Sleep and Wakefulness, *European Journal of Pharmacology*, 205:283–287 (1991).

J. Monti et al., Sleep and Waking During Acute Histamine $H_3$ Agonist BP2.94 or $H_3$ Antagonist Carboperamide (MR 16155) Administration in Rats, *Neuropsychopharmacology*, 15(1):31–35 (1996).

K. Murakami et al., AQ–0145, A Newly Developed Histamine $H_3$ Antagonist, Decreased Seizure Susceptibility of Electrically Induced Convulsions in Mice, *Meth. Find. Exp. Clin. Pharmacol.*, 17(C):70–73 (1995).

K. Onodera et al., Neuropharmacology of the Histaminergic Neuron System in the Brain and Its Relationship with Behavioural Disorders, *Progress in Neurobiology*, 42:685–702 (1994).

M. Airaksinen et al., Histamine Neurons in Human Hypothalamus: Anatomy in Normal and Alzheimer Diseased Brains, *Neuroscience*, 44(2):465–481 (1991).

J. Phillips et al., Recent Advances in Histamine $H_3$ Receptor Agents, *Annual Reports in Medicinal Chemistry*, 33:31–40 (1998).

A. Rouleau, Bioavailability, Antinociceptive and Antiflammatory Properties of BP 2–94, A Histamine $H_3$ Receptor Agonist Prodrug, *The Journal of Pharmacology and Experimental Therapeutics*, 281(3):1085–1094 (1997).

N. Sakai et al., Effects of Thioperamide, A Histamine $H_3$ ReceptorAntagonist, on Locomotor Activity and Brain Histamine Content in Mast Cell–Deficient W/W$^v$ Mice, *Life Sciences*, 48:2397–2404 (1991).

J. Schwartz et al., Histamine, *Psychopharmacology: The Fourth Generation of Progress*, 397–405 (1995).

B. Shaywitz et al., Dopaminergic but not Noradrenergic Mediation of Hyperactivity and Performance Deficits in the Developing Rat Pup, *Psychopharmacology*, 82:73–77 (1984).

A. Szelag, Role of Histamine $H_3$–Receptors in the Proliferation Neoplastic Cells in Vitro, *Med. Sci. Monit.*, 4(5):747–755 (1998).

C. Tedford et al., Cognition and Locomotor Activity in the Developing Rat: Comparisons of Histamine $H_3$ Receptor Antagonists and ADHD Therapeutics, *Society for Neuroscience Abstr.*, 22:22 (1996).

C. Tedford et al., Pharmacological Characterization of GT–2016, a Non–Thiourea–Containing Histamine $H_3$ Receptor Antagonist: In Vitro and In Vivo Studies, *The Journal of Pharmacology and Experimental Therapeutics*, 275(2):598–604 (1995).

H. Wada et al., Is the Histaminergic Neuron System a Regulatory Center for Whole–Brain Activity?, *Trends in Neurosciences*, 14(9):415–418 (1991).

H. Yokoyama et al., Effect of Thioperamide, a Histamine $H_3$ Receptor Antagonist, on Electrically Induced Convulsions in Mice, *Journal of Pharamacology*, 234:129–133 (1993).

H. Yokoyama et al., Histamine and Seizures Implications for the Treatment of Epilepsy, *CNS Drugs*, 5(5):321–330 (1996).

* cited by examiner

AMINOALKOXYBIPHENYLCARBOXAMIDES AS HISTAMINE-3 RECEPTOR LIGANDS AND THEIR THERAPEUTIC APPLICATIONS

TECHNICAL FIELD

This invention relates to compounds of formula (I), which are histamine-3 receptor ligands. This invention also relates to pharmaceutical compositions containing compounds of formula (I) and methods of treatment using compounds of formula (I).

BACKGROUND OF THE INVENTION

Histamine is a well-known mediator in hypersensitive reactions (e.g. allergies, hay fever, and asthma) which are commonly treated with antagonists of histamine or "antihistamines." It has also been established that histamine receptors exist in at least two distinct types, referred to as $H_1$ and $H_2$ receptors.

A third histamine receptor ($H_3$ receptor) is believed to play a role in neurotransmission in the central nervous system, where the $H_3$ receptor is thought to be disposed presynaptically on histaminergic nerve endings (Nature, 302, 832–837 (1983)). The existence of the $H_3$ receptor has been confirmed by the development of selective $H_3$ receptor agonists and antagonists (Nature, 327, 117–123 (1987)) and has subsequently been shown to regulate the release of other neurotransmitters in both the central nervous system and peripheral organs, particularly the lungs, cardiovascular system and gastrointestinal tract.

A number of diseases or conditions may be treated with histamine-3 receptor ligands wherein the $H_3$ ligand may be an antagonist, agonist or partially agonist (Imamura et al., Circ.Res., (1996) 78, 475–481); (Imamura et. al., Circ.Res., (1996) 78, 863–869); (Lin et al., Brain Res. (1990) 523, 325–330); (Monti et al., Neuropsychopharmacology (1996) 15, 31–35); (Sakai, et al., Life Sci. (1991) 48, 2397–2404); (Mazurkiewicz-Kwilecki and Nsonwah, Can. J. Physiol. Pharmacol. (1989) 67, 75–78); (Panula, P. et al., Neuroscience (1998) 44, 465–481); (Wada et al., Trends in Neuroscience (1991) 14, 415); (Monti et al., Fur. J. Pharmacol. (1991) 205, 283); (Mazurkiewicz-Kwilecki and Nsonwah, Can. J. Physiol. Pharmacol. (1989) 67, 75–78); (Haas et al., Behav. Brain Res. (1995) 66, 41–44); (De Almeida and Izquierdo, Arch. Int. Pharmacodyn. (1986) 283, 193–198); (Kamei et al., Psychopharmacology (1990) 102, 312–318); (Kamei and Sakata, Jpn. J. Pharmacol. (1991) 57, 437–482); (Schwartz et al., Psychopharmacology; The fourth Generation of Progress. Bloom and Kupfer (eds). Raven Press, New York, (1995) 397); (Shaywitz et al., Psychopharmacology (1984) 82, 73–77); (Dumery and Blozovski, Exp. Brain Res. (1987) 67, 61–69); (Tedford et al., J. Pharmacol. Exp. Ther. (1995) 275, 598–604); (Tedford et al., Soc. Neurosci. Abstr. (1996) 22, 22); (Yokoyama et al., Eur. J. Pharmacol. (1993) 234, 129); (Yokoyama and Iinuma, CNS Drugs (1996) 5, 321); (Onodera et al., Prog. Neurobiol. (1994) 42, 685); (Leurs and Timmerman, Prog. Drug Res. (1992) 39, 127); (The Histamine $H_3$ Receptor, Leurs and Timmerman (eds), Elsevier Science, Amsterdam, The Netherlands (1998); (Leurs et al., Trends in Pharm. Sci. (1998) 19, 177–183); (Phillips et al., Annual Reports in Medicinal Chemistry (1998) 33, 31–40); (Matsubara et al., Eur. J. Pharmacol. (1992) 224, 145); (Rouleau et al., J. Pharmacol. Exp. Ther. (1997) 281, 1085); (Adam Szelag, "Role of histamine $H_3$-receptors in the proliferation of neoplastic cells in vitro", Med. Sci. Monit., 4(5): 747–755, (1998)); (Fitzsimons, C., H. Duran, F. Labombarda, B. Molinari and E. Rivera, "Histamine receptors signalling in epidermal tumor cell lines with H-ras gene alterations", Inflammation Res., 47 (Suppl 1): S50-S51, (1998)); (R. Leurs, R. C. Vollinga and H. Timmerman, "The medicinal chemistry and therapeutic potentials of ligand of the histamine $H_3$ receptor", Progress in Drug Research 45: 170–165, (1995)); (R. Levi and N. C. E. Smith, "Histamine $H_3$-receptors: A new frontier in myocardial ischemia", J. Pharm. Exp. Ther., 292: 825–830, (2000)); (Hatta, E., K Yasuda and R. Levi, "Activation of histamine $H_3$ receptors inhibits carrier-mediated norepinephrine release in a human model of protracted myocradial ischemia", J. Pharm. Exp. Ther., 283: 494–500, (1997); (H. Yokoyama and K. Iinuma, "Histamine and Seizures: Implications for the treatment of epilepsy", CNS Drugs, 5(5); 321–330, (1995)); (K. Hurukami, H. Yokoyama, K. Onodera, K. Iinuma and T. Watanabe, AQ-0145, "A newly developed histamine $H_3$ antagonist, decreased seizure susceptibility of electrically induced convulsions in mice", Meth. Find. Exp. Clin. Pharmacol., 17(C): 70–73, (1995); (Delaunois A., Gustin P., Garbarg M., and Ansay M., "Modulation of acetylcholine, capsaicin and substance P effects by histamine $H_3$ receptors in isolated perfused rabbit lungs", European Journal of Pharmacology 277(2–3): 243–50, (1995)); and (Dimitriadou, et al., "Functional relationship between mast cells and C-sensitive nerve fibres evidenced by histamine $H_3$-receptor modulation in rat lung and spleen", Clinical Science. 87(2):151–63, (1994). Such diseases or conditions include cardiovascular disorders such as acute myocardial infarction; memory processes, dementia and cognition disorders such as Alzheimer's disease and attention-deficit hyperactivity disorder; neurological disorders such as Parkinson's disease, schizophrenia, depression, epilepsy, and seizures or convulsions; cancer such as cutaneous carcinoma, medullary thyroid carcinoma and melanoma; respiratory disorders such as asthma; sleep disorders such as narcolepsy; vestibular dysfunction such as Meniere's disease; gastrointestinal disorders, inflammation, migraine, motion sickness, obesity, pain, and septic shock.

WO 00/06254 describes non-imidazole alkylamines as histamine-3 receptor ligands. EP 0 978 512 Al describes non-imidazole aryloxy alkylamines as histamine-3 receptor ligands.

SUMMARY OF THE INVENTION

In its principle embodiment, the present invention discloses compounds of formula (I):

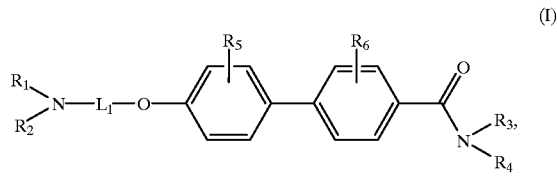

or a pharmaceutically acceptable salt thereof, wherein $L_1$ is alkylene;

$R_1$ and $R_2$ are each independently selected from the group consisting of hydrogen, alkyl, aryl, arylalkyl, cycloalkyl, cycloalkylalkyl, heterocycle and heterocyclealkyl; or $R_1$ and $R_2$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl;

$R_3$ and $R_4$ are each independently selected from the group consisting of hydrogen, alkyl, aryl, arylalkyl, cycloalkyl, cycloalkylalkyl, heterocycle and heterocyclealkyl; or $R_3$ and $R_4$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; and $R_5$ and $R_6$ are each independently selected from the group consisting of hydrogen, alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$) sulfonyl;

provided that when $R_1$ and $R_2$ together form pyrrolidinyl and wherein said pyrrolidinyl is substituted with 1 substituent then said substituent is other than alkoxy, hydroxy or —$NR_AR_B$.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the present invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the present invention, may be made without departing from the spirit and scope thereof.

In its principle embodiment, the present invention discloses compounds of formula (I):

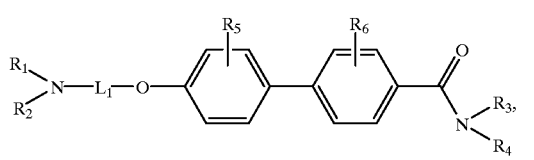

(I)

or a pharmaceutically acceptable salt thereof, wherein $L_1$ is alkylene;

$R_1$ and $R_2$ are each independently selected from the group consisting of hydrogen, alkyl, aryl, arylalkyl, cycloalkyl, cycloalkylalkyl, heterocycle and heterocyclealkyl; or $R_1$ and $R_2$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl;

$R_3$ and $R_4$ are each independently selected from the group consisting of hydrogen, alkyl, aryl, arylalkyl, cycloalkyl, cycloalkylalkyl, heterocycle and heterocyclealkyl; or $R_3$ and $R_4$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; and $R_5$ and $R_6$ are each independently selected from the group consisting of hydrogen, alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$) carbonyl and ($NR_AR_B$)sulfonyl;

provided that when $R_1$ and $R_2$ together form pyrrolidinyl and wherein said pyrrolidinyl is substituted with 1 substituent then said substituent is other than alkoxy, hydroxy or —$NR_AR_B$.

In a preferred embodiment, compounds of the present invention have formula (I) wherein $L_1$ is —$CH_2CH_2CH_2$—; $R_1$ and $R_2$ are each independently selected from hydrogen, alkyl, arylalkyl and heterocycle; or $R_1$ and $R_2$ taken together with the nitrogen atom to which they are attached, together form a heterocycle selected from morpholinyl, piperidinyl and pyrrolidinyl; $R_3$ and $R_4$ are each independently selected from hydrogen and alkyl; or $R_3$ and $R_4$ taken together with the nitrogen atom to which they are attached, together form a heterocycle selected from morpholinyl, piperidinyl and pyrrolidinyl; and $R_5$ and $R_6$ are as defined in formula (I).

In a preferred embodiment, compounds of the present invention have formula (I) wherein $L_1$ is —$CH_2CH_2CH_2$—; $R_1$ and $R_2$ are each independently selected from hydrogen, alkyl, arylalkyl and heterocycle; or $R_1$ and $R_2$ taken together with the nitrogen atom to which they are attached, together form a heterocycle selected from morpholinyl, piperidinyl and pyrrolidinyl; $R_3$ and $R_4$ are each independently selected from hydrogen and alkyl; or $R_3$ and $R_4$ taken together with the nitrogen atom to which they are attached, together form a heterocycle selected from morpholinyl, piperidinyl and pyrrolidinyl; and $R_5$ and $R_6$ are each hydrogen.

In another preferred embodiment, compounds of the present invention have formula (I) wherein $L_1$ is selected from —$CH_2CH_2$— and —$CH_2CH_2CH_2$—; $R_1$ and $R_2$ are each independently selected from hydrogen, alkyl, aryl, arylalkyl, cycloalkyl, cycloalkylalkyl, heterocycle and heterocyclealkyl; $R_3$ and $R_4$ are each independently selected from hydrogen, alkyl, aryl, arylalkyl, cycloalkyl, cycloalkylalkyl, heterocycle and heterocyclealkyl; and $R_5$ and $R_6$ are as defined in formula (I).

In another preferred embodiment, compounds of the present invention have formula (I) wherein $L_1$ is —$CH_2CH_2CH_2$—; $R_1$ and $R_2$ are each independently selected from hydrogen, alkyl, arylalkyl and heterocycle; $R_3$ and $R_4$ are each independently selected from hydrogen and alkyl; and $R_5$ and $R_6$ arc as defined in formula (I).

In another preferred embodiment, compounds of the present invention have formula (I) wherein $L_1$ is —$CH_2CH_2CH_2$—; $R_1$ and $R_2$ are each independently selected from hydrogen, alkyl, arylalkyl and heterocycle; $R_3$ and $R_4$ are each independently selected from hydrogen and alkyl; and $R_5$ and $R_6$ are each hydrogen.

In another preferred embodiment, compounds of the present invention have formula (I) wherein $L_1$ is selected from —$CH_2CH_2$— and —$CH_2CH_2CH_2$—; $R_1$ and $R_2$ taken together with the nitrogen atom to which they are attached, together form a heterocycle selected from azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; $R_3$ and $R_4$ are each independently selected from the group consisting of hydrogen, alkyl, aryl, arylalkyl, cycloalkyl, cycloalkylalkyl, heterocycle and heterocyclealkyl; and $R_5$ and $R_6$ are as defined in formula (I).

In another preferred embodiment, compounds of the present invention have formula (I) wherein $L_1$ is —$CH_2CH_2CH_2$—; $R_1$ and $R_2$ taken together with the nitrogen atom to which they are attached, together form a heterocycle selected from morpholinyl, piperidinyl and pyrrolidinyl; $R_3$ and $R_4$ are each independently selected from the group consisting of hydrogen and alkyl; and $R_5$ and $R_6$ are as defined in formula (I).

In another preferred embodiment, compounds of the present invention have formula (I) wherein $L_1$ is —$CH_2CH_2CH_2$—; $R_1$ and $R_2$ taken together with the nitrogen atom to which they are attached, together form a heterocycle selected from morpholinyl, piperidinyl and pyrrolidinyl; $R_3$ and $R_4$ are each independently selected from the group consisting of hydrogen and alkyl; and $R_5$ and $R_6$ are each hydrogen.

In another preferred embodiment, compounds of the present invention have formula (I) wherein $L_1$ is selected from —$CH_2CH_2$— and —$CH_2CH_2CH_2$—; $R_{and\ R2}$ are each independently selected from hydrogen, alkyl, aryl, arylalkyl, cycloalkyl, cycloalkylalkyl, heterocycle and heterocyclealkyl; $R_3$ and $R_4$ taken together with the nitrogen atom to which they are attached, together form a heterocycle selected from azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; and $R_5$ and $R_6$ are as defined in formula (I).

In another preferred embodiment, compounds of the present invention have formula (I) wherein $L_1$ is —$CH_2CH_2CH_2$—; $R_1$ and $R_2$ are each independently selected from hydrogen, alkyl, arylalkyl and heterocycle; $R_3$ and $R_4$ taken together with the nitrogen atom to which they are attached, together form a heterocycle selected from morpholinyl, piperidinyl and pyrrolidinyl; and $R_5$ and $R_6$ are as defined in formula (I).

In another preferred embodiment, compounds of the present invention have formula (I) wherein $L_1$ is —$CH_2CH_2CH_2$—; $R_1$ and $R_2$ taken together with the nitrogen atom to which they are attached, together form a heterocycle selected from morpholinyl, piperidinyl and pyrrolidinyl; $R_3$ and $R_4$ are each independently selected from the group consisting of hydrogen and alkyl; and $R_5$ and $R_6$ are each hydrogen.

In another preferred embodiment, compounds of the present invention have formula (I) wherein $L_1$ is selected from —$CH_2CH_2$— and —$CH_2CH_2CH_2$—; $R_1$ and $R_2$ taken together with the nitrogen atom to which they are attached, together form a heterocycle selected from azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; $R_3$ and $R_4$ taken together with the nitrogen atom to which they are attached, together form a heterocycle selected from azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; and $R_5$ and $R_6$ are as defined in formula (I).

In another preferred embodiment, compounds of the present invention have formula (I) wherein $L_1$ is —$CH_2CH_2CH_2$—; $R_1$ and $R_2$ taken together with the nitrogen atom to which they are attached, together form a heterocycle selected from the group consisting of morpholinyl, piperidinyl and pyrrolidinyl; $R_3$ and $R_4$ taken together with the nitrogen atom to which they are attached, together form a heterocycle selected from the group consisting of morpholinyl, piperidinyl and pyrrolidinyl; and $R_5$ and $R_6$ are as defined in formula (I).

In another preferred embodiment, compounds of the present invention have formula (I) wherein $L_1$ is —$CH_2CH_2CH_2$—; $R_1$ and $R_2$ taken together with the nitrogen atom to which they are attached, together form a heterocycle selected from the group consisting of morpholinyl, piperidinyl and pyrrolidinyl; $R_3$ and $R_4$ taken together with the nitrogen atom to which they are attached, together form a heterocycle selected from the group consisting of morpholinyl, piperidinyl and pyrrolidinyl; and $R_5$ and $R_6$ are each hydrogen.

Another embodiment of the present invention relates to pharmaceutical compositions comprising a therapeutically effective amount of a compound of formula (I) or a pharmaceutically acceptable salt, ester, amide, or prodrug thereof in combination with a pharmaceutically acceptable carrier.

Another embodiment of the present invention relates to a method of modulating the effects of the histamine-3 receptor in a mammal comprising administering a therapeutically effective amount of a compound of formula (I) or a pharmaceutically acceptable salt, ester, amide, or prodrug thereof in combination with a pharmaceutically acceptable carrier.

Another embodiment of the present invention relates to a method of treating acute myocardial infarction, Alzheimer's disease, asthma, attention-deficit hyperactivity disorder, cutaneous carcinoma, depression, epilepsy, inflammation, medullary thyroid carcinoma, melanoma, Meniere's disease, migraine, motion sickness, narcolepsy, obesity, pain, Parkinson's disease, schizophrenia, seizures or septic shock comprising administering a therapeutically effective amount of a compound of formula (I) or a pharmaceutically acceptable salt, ester, amide, or prodrug thereof in combination with a pharmaceutically acceptable carrier.

Definition of Terms

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl and 3-decenyl.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy and hexyloxy.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy and methoxymethoxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy and tert-butylcarbonyloxy.

The term "alkylene," denotes a divalent group derived from a straight or branched chain hydrocarbon of from 2 to 10 carbon atoms. Representative examples of alkylene include, but are not limited to, —CH$_2$CH$_2$—, —CH$_2$CH$_2$CH$_2$—, —CH(CH$_2$CH$_3$)CH$_2$CH$_2$—, —CH$_2$CH$_2$CH(CH$_3$)—, —CH(CH$_3$)CH$_2$CH$_2$—, —CH(CH$_3$)CH(CH$_3$)CH$_2$—, —C(CH$_3$)$_2$CH$_2$—, —CH$_2$CH(CH$_3$)CH$_2$—, —CH$_2$CH$_2$CH$_2$CH$_2$— and —CH$_2$CH$_2$CH$_2$CH$_2$CH$_2$—.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, ethylsulfonyl, isopropylsulfonyl and methylsulfonyl.

The term "alkylthio," as used herein, refers to an alkyl group, as defined herein, appended to the parent molecular moiety through a sulfur atom, as defined herein. Representative examples of alkylthio include, but are not limited to, methylsulfanyl, ethylsulfanyl, tert-butylsulfanyl and hexylsulfanyl.

The term "alkynyl," as used herein, refers to a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl and 1-butynyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 1, 2, or 3 substituents independently selected from alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl and (NR$_A$R$_B$)sulfonyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl and 3-cyanopropyl.

The term "cycloalkyl," as used herein, refers to a saturated cyclic hydrocarbon group containing from 3 to 8 carbons. Examples of cycloalkyl include cyclopropyl, cyclobutyl, cyclopentyl, cyclohexyl, cycloheptyl and cyclooctyl.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl.

The term "formyl," as used herein, refers to a —C(O)H group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic or bicyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, 2,5-dihydro-1H-pyrrolyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic heterocyclic ring systems fused to an aryl group as defined herein, a cycloalkyl group as defined herein, or another monocyclic heterocyclic ring system. Representative examples of bicyclic ring systems include but are not limited to, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl.

The heterocycles of this invention can be substituted with 1, 2, or 3 substituents independently selected from alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, arylalkyl, carboxy, carboxyalkyl, cyano, cyanoalkyl, formyl, halogen, haloalkoxy, haloalkyl, hydroxy, hydroxyalkyl, mercapto, nitro, oxo, —NR$_A$R$_B$, (NR$_A$R$_B$)alkyl, (NR$_A$R$_B$)carbonyl and (NR$_A$R$_B$)sulfonyl.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "hydroxy," as used herein, refers to an —OH group.

The term "hydroxyalkyl," as used herein, refers to one or two hydroxy groups, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypropyl and 2-ethyl-4-hydroxyheptyl.

The term "mercapto," as used herein, refers to a —SH group.

The term "nitro," as used herein, refers to a —NO$_2$ group.

The term "—NR$_A$R$_B$," as used herein, refers to two groups, R$_A$ and R$_B$, which are appended to the parent molecular moiety through a nitrogen atom. R$_A$ and R$_B$ are each independently selected from hydrogen, alkyl, alkylcarbonyl and formyl. Representative examples of —NR$_A$R$_B$ include, but are not limited to, acetylamino, amino, formylamino, dimethylamino and methylamino.

The term "(NR$_A$R$_B$)alkyl," as used herein, refers to a —NR$_A$R$_B$ group, as defined herein, appended to the parent molecular moiety through an alkyl group, as defined herein. Representative examples of (NR$_A$R$_B$)alkyl include, but are not limited, (amino)methyl, (dimethylamino)methyl and (ethylamino)methyl.

The term "(NR$_A$R$_B$)carbonyl," as used herein, refers to a —NR$_A$R$_B$ group, as defined herein, appended to the parent molecular moiety through a carbonyl group, as defined herein. Representative examples of (NR$_A$R$_B$)carbonyl include, but are not limited, aminocarbonyl, dimethylaminocarbonyl and ethylaminocarbonyl.

The term "(NR$_A$R$_B$)sulfonyl," as used herein, refers to an amino group, as defined herein, appended to the parent molecular moiety through a sulfonyl group, as defined herein. Representative examples of aminosulfonyl include, but are not limited, aminosulfonyl, dimethylaminosulfonyl and ethylaminosulfonyl.

The term "oxo," as used herein, refers to a =O moiety.

The term "oxy," as used herein, refers to a —O— moiety.

The term "sulfinyl," as used herein, refers to a —S(O)— group.

The term "sulfonyl," as used herein, refers to a —SO$_2$— group.

Preferred compounds of formula (I) include, but are not limited to:

4'-{3-[(2R,5R)-2,5-dimethylpyrrolidinyl]propoxy}-N-isopropyl[1,1'-biphenyl]-4-carboxamide;

4'-{3-[(2R,5R)-2,5-dimethylpyrrolidinyl]propoxy}-N,N-diethyl[1,1'-biphenyl]-4-carboxamide;

(2R,5R)-2,5-dimethyl-1-[3-({4'-[(2-methyl-1-pyrrolidinyl)carbonyl][1,1'-biphenyl]-4-yl}oxy)propyl]pyrrolidine;

3-[(4'-{[(2R,5R)-2,5-dimethylpyrrolidinyl]carbonyl}[1,1'-biphenyl]-4-yl)oxy]-N-isopropyl-1-propanamine;

3-[(4'-{[(2R,5R)-2,5-dimethylpyrrolidinyl]carbonyl}[1,1'-biphenyl]-4-yl)oxy]-N,N-diethyl-1-propanamine;

(2R,5R)-1-[(4'-{3-[(2R,5R)-2,5-dimethylpyrrolidinyl]propoxy}[1,1'-biphenyl]-4-yl)carbonyl]-2,5-dimethylpyrrolidine;

1-{3-[(4'-{[(2R,5R)-2,5-dimethylpyrrolidinyl]carbonyl}[1,1'-biphenyl]-4-yl)oxy]propyl}-4-methylpiperidine;

4-{3-[(4'-{[(2R,5R)-2,5-dimethylpyrrolidinyl]carbonyl}[1,1'-biphenyl]-4-yl)oxy]propyl}morpholine;

1-[(4'-{3-[(2R,5R)-2,5-dimethylpyrrolidinyl]propoxy}[1,1'-biphenyl]-4-yl)carbonyl]-4-methylpiperidine;

N-methyl-N-[(1R)-1-phenylethyl]-N-(3-{[4'-(1-pyrrolidinylcarbonyl)[1,1'-biphenyl]-4-yl]oxy}propyl)amine;

N-[(3R)-1-benzylpyrrolidinyl]-N-methyl-N-(3-{[4'-(1-pyrrolidinylcarbonyl)[1,1'-biphenyl]-4-yl]oxy}propyl)amine;

[(2R)-1-(3-{[4'-(1-pyrrolidinylcarbonyl)[1,1'-biphenyl]-4-yl]oxy}propyl)pyrrolidinyl]methanol;

[(2S)-1-(3-{[4'-(1-pyrrolidinylcarbonyl)[1,1'-biphenyl]-4-yl]oxy}propyl)pyrrolidinyl]methanol;

(2R,6S)-2,6-dimethyl-1-(3-{[4'-(1-pyrrolidinylcarbonyl)[1,1'-biphenyl]-4-yl]oxy}propyl)piperidine;

(3R)-1-(3-{[4'-(1-pyrrolidinylcarbonyl)[1,1-biphenyl]-4-yl]oxy}propyl)-3-piperidinol and pharmaceutically acceptable salts, esters, amides, or prodrugs thereof.

More preferred compounds of formula (I) include, but are not limited to:

4-[(4'-{3-[(2R,5R)-2,5-dimethylpyrrolidinyl]propoxy}[1,1'-biphenyl]-4-yl)carbonyl]morpholine and pharmaceutically acceptable salts, esters, amides, or prodrugs thereof.

Abbreviations

Abbreviations which may have been used in the descriptions of the schemes and the examples that follow are: Boc for tert-butoxycarbonyl; (Boc)$_2$O for di-tert-butyl dicarbonate; DMAP for 4-dimethylaminopyridine; DMF for N,N-dimethylformamide; DMSO for dimethyl sulfoxide; EtOAc for ethyl acetate; EtOH for ethanol; LDA for lithium diisopropylamide; MeOH for methanol; pyr for pyridine; TFA for trifluoroacetic acid; and THF for tetrahydrofuran.

Preparation of Compounds of the Invention

The compounds and processes of the present invention will be better understood in connection with the following synthetic schemes and examples which illustrate a means by which the compounds of the present invention can be prepared.

The compounds of this invention can be prepared by a variety of synthetic routes. A representative procedure is shown in Scheme 1.

as described in Scheme 1. Compounds of general formula (I), which may be purchase or prepared using standard chemistry known to those in the art, may be treated with sulfuric acid in methanol to provide esters of general formula (2). Esters of general formula (2) may be treated with 1-bromo-3-chloropropane (or 1-bromo-2-chloroethane to provide the ethoxy analogues or still another appropriate bromo-chloroalkane to provide analogues as defined in formula (I)), potassium carbonate, and potassium iodide in 2-butanone at reflux for about 24 hours to provide chlorides of general formula (3). Chlorides of general formula (3) may be treated with lithium hydroxide in THF:H$_2$O (3:1) to provide the crude acids. The crude acids may be treated with thionyl chloride (used as solvent) and heat (about 90° C.) for about 4 hours in to provide acid chlorides of general formula (4). Acid chlorides of general formula (4) may be treated with a base such as triethylamine and amines of general

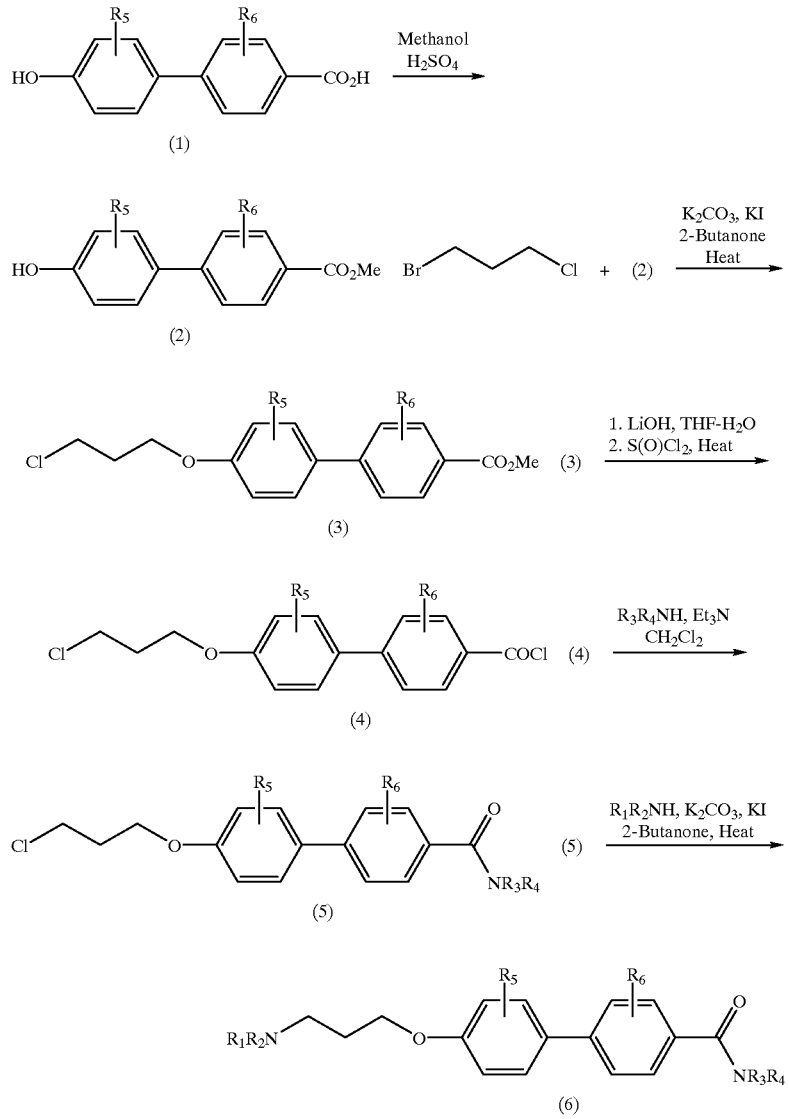

Compounds of general formula (6), wherein R$_1$, R$_2$, R$_3$, R$_4$, R$_5$ and R$_6$ are as defined in formula (I), may be prepared formula R$_3$R$_4$NH in a solvent such as methylene chloride to provide amides of general formula (5). Amides of general formula (5) may be treated with a base such as potassium carbonate, potassium iodide and a base of general formula $R_1R_2NH$ in a solvent such as 2-butanone with heat to provide compounds of general formula (6).

The compounds and processes of the present invention will be better understood by reference to the following examples, which are intended as an illustration of and not a limitation upon the scope of the present invention. Further, all citations herein are incorporated by reference.

EXAMPLE 1

4'-{3-[(2R,5R)-2,5-dimethylpyrrolidinyl]propoxy}-N-isopropyl[1,1'-biphenyl]-4-carboxamide

EXAMPLE 1A

4'-(3-chloropropoxy)-N-isopropyl[1,1'-biphenyl]-4-carboxamide

The product from Example 10D and isopropylamine were processed as described in Example 10 to provide the title compound.

EXAMPLE 1B

4'-{3-[(2R,5R)-2,5-dimethylpyrrolidinyl]propoxy}-N-isopropyl[1,1'-biphenyl]-4-carboxamide The product from Example 1A and (2R,5R)-2,5-dimethylpyrrolidine hydrochloride were processed as described in Example 10F to provide the title compound.
$^1$H NMR (500 MHz, CDCl$_3$) δ1.28 (d, 6H, J=6.5 Hz), 1.31 (d, 3H, J=6.9 Hz), 1.55 (d, 3H, J=6.5 Hz), 1.72 (m, 1H), 1.89 (m, 1H), 1.96–2.19 (m, 5H), 2.28 (m, 2H), 2.46 (m, 2H), 3.07 (m, 1H), 3.33 (m, 2H), 4.07 (m, 1H), 4.16 (m, 1H), 4.29 (m, 2H), 5.93 (m, 1H), 6.95 (d, 2H, J=8.8 Hz), 7.54 (d, 2H, J=8.8 Hz), 7.60 (d, 2H, J=8.5 Hz), 7.80 (d, 2H, J=8.1 Hz); MS (APCI) m/z 395 (M+H)$^+$.

EXAMPLE 2

4'-{3-[(2R,5R)-2,5-dimethylpyrrolidinyl]propoxy}-N,N-diethyl[1,1'-biphenyl]-4-carboxamide

EXAMPLE 2A

4'-(3-chloropropoxy)-N,N-diethyl[1,1'-biphenyl]-4-carboxamide

The product from Example 10D and diethylamine were processed as described in Example 10E to provide the title compound.

EXAMPLE 2B

4'-{3-[(2R,5R)-2,5-dimethylpyrrolidinyl]propoxy}-N,N-diethyl[1,1'-biphenyl]-4-carboxamide The product from Example 2A and (2R,5R)-2,5-dimethylpyrrolidine hydrochloride were processed as described in Example 10F to provide the title compound.
$^1$H NMR (500 MHz, CDCl$_3$) δ1.03–1.29 (m, 6H), 1.31 (d, 3H, J=6.9 Hz), 1.55 (d, 3H, J=6.6 Hz), 1.59 (m, 2H), 1.73 (m, 1H), 1.90 (m, 1H), 2.28 (m, 3H), 2.46 (m, 3H), 3.08 (m, 1H), 3.35 (m, 4H), 3.57 (m, 2H), 4.08 (m, 1H), 4.17 (m, 1H), 4.25 (m, 1H), 6.95 (d, 2H, J=8.8 Hz), 7.43 (d, 2H, J=8.1 Hz), 7.53 (d, 2H, J=8.7 Hz), 7.56 (d, 2H, J=8.1 Hz); MS (APCI) m/z 409 (M+H)$^+$.

EXAMPLE 3

(2R,5R)-2,5-dimethyl-1-[3-({4'-[(2-methyl-1-pyrrolidinyl)carbonyl][1,1'-biphenyl]-4-yl}oxy)propyl]pyrrolidine

EXAMPLE 3A

1-{[4'-(3-chloropropoxy)[1,1'-biphenyl]-4-yl]carbonyl}-2-methylpyrrolidine

The product from Example 10D and 2-methylpyrrolidine were processed as described in Example 10E to provide the title compound.

EXAMPLE 3B (2R,5R)-2,5-dimethyl-1-[3-({4'-[(2-methyl-1-pyrrolidinyl)carbonyl][1,1'-yl}oxy)propyl] pyrrolidine The product from Example 3A and (2R,5R)-2,5-dimethylpyrrolidine hydrochloride were processed as described in Example 10F to provide the title compound.
$^1$H NMR (500 MHz, CDCl$_3$) δ1.31 (d, 3H, J=6.9 Hz), 1.38 (d, 3H, J=4.1 Hz), 1.55 (d, 3H, J=6.6 Hz), 1.64 (m, 1H), 1.76 (m, 2H), 1.90 (m, 2H), 2.17 (m, 1H), 2.29 (m, 2H), 2.47 (m, 2H), 2.72–3.00 (m, 5H), 3.08 (m, 2H), 3.33 (m, 2H), 3.51 (m, 2H), 4.08 (m, 1H), 4.16 (m, 1H), 4.25 (m, 1H), 4.36 (m, 1H), 6.95 (m, 2H), 7.55 (m, 6H); MS (APCI) m/z 421 (M+H)$^+$.

EXAMPLE 4

3-[(4'-{[(2R,5R)-2,5-dimethylpyrrolidinyl]carbonyl}[1,1'-biphenyl]-4-yl)oxy]-N-isopropyl-1-propanamine

EXAMPLE 4A (2R,5R)-1-{[4'-(3-chloropropoxy)[1,1'-biphenyl]-4-yl]carbonyl}-2,5-dimethylpyrrolidine The product from Example 10D and (2R,5R)-2,5-dimethylpyrrolidine hydrochloride were processed as described in Example 10E to provide the title compound.

EXAMPLE 4B

3-[(4'-{[(2R,5R)-2,5-dimethylpyrrolidinyl]carbonyl}[1,1'-biphenyl]-4-yl)oxy]-N-isopropyl-1-propanamine The product from Example 4A and isopropylamine were processed as described in Example 10F to provide the title compound.
$^1$H NMR (500 MHz, CDCl$_3$) δ0.84 (d, 3H, J=6.2 Hz), 1.27 (m, 1H), 1.31 (d, 3H, J=6.2 Hz), 1.39 (d, 6H, J=6.6 Hz), 1.61 (m, 2H), 1.97–2.47 (m, 11H), 3.18 (m, 2H), 3.55 (m, 1H), 4.07 (m, 2H), 4.20 (m, 1H), 4.48 (m, 1H), 6.92 (m, 2H), 7.52 (m, 6H); MS (APCI) m/z 395 (M+H)$^+$.

EXAMPLE 5

3-[(4'-{[(2R,5R)-2,5-dimethylpyrrolidinyl]carbonyl}[1,1'-biphenyl]-4-yl)oxy]-N,N-diethyl-1-propanamine The product from Example 4A and diethylamine were processed as described in Example 10F to provide the title compound.
$^1$H NMR (500 MHz, CDCl$_3$) δ0.85 (d, 3H, J=6.2 Hz), 1.32 (d, 3H, J=6.3 Hz), 1.38 (t, 6H, J=7.1 Hz), 1.62 (m, 2H), 2.15 (m, 1H), 2.28 (m, 4H), 2.33–2.55 (m, 5H), 3.20 (m, 4H), 3.29 (m, 2H), 4.12 (m, 2H), 4.22 (m, 1H), 4.48 (m, 1H), 6.96 (m, 2H), 7.54 (m, 6H); MS (APCI) m/z 409 (M+H)$^+$.

EXAMPLE 6

(2R,5R)-1-[(4'-{3-[(2R,5R)-2,5-dimethylpyrrolidinyl]propoxy}[1,1'-biphenyl]-4-yl)carbonyl]-2,5-dimethylpyrrolidine The product from Example 4A and (2R,5R)-2,5-dimethylpyrrolidine hydrochloride were processed as described in Example 10F to provide the title compound.

¹H NMR (500 MHz, CDCl₃) δ0.85 (d, 3H, J=6.3 Hz), 1.31 (d, 3H, J=6.8 Hz), 1.32 (d, 3H, J=5.0 Hz), 1.56 (d, 3H, J=6.5 Hz), 1.61 (m, 2H), 1.73 (m, 1H), 1.90 (m, 1H), 2.16 (m, 1H), 2.29 (m, 3H), 2.48 (m, 3H), 3.08 (m, 1H), 3.34 (m, 2H), 4.08 (m, 1H), 4.16 (m, 1H), 4.24 (m, 2H), 4.49 (m, 1H), 6.95 (m, 2H), 7.53 (m, 6H); MS (APCI) m/z 435 (M+H)⁺.

EXAMPLE 7

1-{3-[(4'-{[(2R,5R)-2,5-dimethylpyrrolidinyl]carbonyl}[1,1'-biphenyl]-4-yl)oxy]propyl}-4-methylpiperidine The product from Example 4A and 4-methylpiperidine were processed as described in Example 10F to provide the title compound.

¹H NMR (500 MHz, CDCl₃) δ0.85 (d, 3H, J=6.2 Hz), 1.04 (d, 3H, J=6.6 Hz), 1.32 (d, 3H, J=6.3 Hz), 1.60 (m, 3H), 1.76 (m, 2H), 1.86 (m, 2H), 2.16 (m, 1H), 2.22–2.45 (m, 8H), 3.22 (m, 2H), 3.70 (m, 2H), 4.11 (m, 2H), 4.21 (m, 1H), 4.48 (m, 1H), 6.94 (m, 2H), 7.54 (m, 6H); MS (APCI) m/z 435 (M+H)⁺.

EXAMPLE 8

4-{3-[(4'-{(2R,5R)-2,5-dimethylpyrrolidinyl]carbonyl}[1,1'-biphenyl]-4-yl)oxy]propyl}morpholine The product from Example 4A and morpholine were processed as described in Example 10F to provide the title compound.

¹H NMR (500 MHz, CDCl₃) δ0.85 (d, 3H, J=6.6 Hz), 1.32 (d, 3H, J=6.3 Hz), 1.61 (m, 2H), 2.16 (m, 1H), 2.29 (m, 3H), 2.91 (m, 3H), 3.28 (m, 2H), 3.61 (m, 2H), 4.02 (m, 4H), 4.12 (m, 2H), 4.22 (m, 1H), 4.49 (m, 1H), 6.94 (d, 2H, J=8.8 Hz), 7.54 (m, 6H); MS (APCI) m/z 423 (M+H)⁺.

EXAMPLE 9

1-[(4'-{3-[(2R,5R)-2,5-dimethylpyrrolidinyl]propoxy}[1,1'-biphenyl[-4-yl)carbonyl]-4-methylpiperidine

EXAMPLE 9A

1-{[4'-(3-chloropropoxy)[1,1'-biphenyl]-4-yl]carbonyl}-4-methylpiperidine

The product from Example 10D and 4-methylpiperidine were processed as described in Example 10E to provide the title compound.

EXAMPLE 9B

1-[(4'-{3-[(2R,5R)-2,5-dimethylpyrrolidinyl]propoxy}[1,1'-biphenyl]-4-yl)carbonyl]-4-methylpiperidine The product from Example 9A and (2R,5R)-2,5-dimethylpyrrolidine hydrochloride were processed as described in Example 10F to provide the title compound.

¹H NMR (500 MHz, CDCl₃) δ0.99 (d, 3H, J=6.5 Hz), 1.31 (d, 3H, J=6.9 Hz), 1.56 (d, 3H, J=6.5 Hz), 6.95 (d, 2H, J=8.8 Hz), 7.44 (d, 2H, J=8.1 Hz), 7.53 (d, 2H, J=8.8 Hz), 7.56 (d, 2H, J=8.4 Hz); MS (APCI) m/z 435 (M+H)⁺.

EXAMPLE 10

4-[(4'-{3-[(2R,5R)-2,5-dimethylpyrrolidinyl]propoxy}[1,1'-biphenyl]-4-yl)carbonyl]morpholine

EXAMPLE 10A methyl 4'-hydroxy[1,1'-biphenyl]-4-carboxylate

4'-Hydroxy[1,1'-biphenyl]-4-carboxylic acid (5.0 g, 23.34 mmol, purchased from Aldrich Chemical Co.) and sulfuric acid (0.5 mL) in methanol (100 mL) were heated at reflux temperature for 24 hours. The mixture was allowed to cool to ambient temperature and then filtered. The filter cake was washed with cold methanol (2×25 mL) and dried under reduced pressure to provide the title compound (95% yield).

¹H NMR (300 MHz, DMSO-d₆) δ9.7 (s, 1H), 7.9 (d, 2H), 7.7 (d, 2H), 7.5 (d, 2H), 6.8 (d, 2H), 3.8 (s, 3H); MS (CI) 246 (M+NH₄)⁺.

EXAMPLE 10B methyl 4'-(3-chloropropoxy)[1,1'-biphenyl]-4-carboxylate

The product from Example 10A (4.50 g, 19.7 mmol), K₂CO₃ (4.0 g, 29.6 mmol) and 3-bromochloropropane (3.88 g, 24.6 mmol) in 2-butanone (100 mL) were heated at reflux for 24 hours. The mixture was allowed to cool to ambient temperature and then diluted with ethyl acetate (200 mL). The mixture was washed with water (2×100 mL) and brine (100 mL) and the remaining organic layer was dried over MgSO₄ and filtered. The filtrate was evaporated under reduced pressure to provide the title compound as an off-white solid (5.5 g, 92% yield).

¹H NMR (300 MHz, DMSO-d₆) δ8.0 (d, 2H), 7.8 (d, 2H), 7.6 (d, 2H), 7.0 (d, 2H), 4.1 (t, J=6.3 Hz, 2H), 3.8 (t, J=6.3 Hz, 2H), 2.2 (m, 2H); MS (CI) 305 (M+H)⁺, 322 (M+NH₄)⁺.

EXAMPLE 10C

4'-(3-chloropropoxy)[1,1'-biphenyl]-4-carboxylic acid

The product from Example 10B (3.4 g, 11.2 mmol) and lithium hydroxide (1.2 g, 28.6 mmol) in THF:water (3:1, 52 mL) were stirred vigorously at ambient temperature for 24 hours. The volume of the mixture was reduced under reduced pressure and then extracted with hexanes (2×25 mL). The remaining aqueous phase was acidified to pH 2 and then extracted with ethyl acetate (3×50 mL). The ethyl acetate extract was evaporated under reduced pressure to provide the title compound as a solid (2.68 g).

¹H NMR (300 MHz, MeOD) δ8.0 (d, 2H), 7.7 (d, 2H), 7.6 (d, 2H), 7.0 (d, 2H), (d, 2H), 4.1 (t, J=6 Hz, 2H), 3.7 (d, 2H), 2.2 (m, 2H); MS (CI) 308 (M+NH₄)⁺.

EXAMPLE 10D

4'-(3-chloropropoxy)[1,1'-biphenyl]-4-carbonyl chloride

The product from Example 10C (3.5 g, 11.36 mmol) in thionyl chloride (25 mL) was heated at 90° C. for 4 hours. The solution was allowed to cool to ambient temperature and then the mixture was evaporated to dryness to provide the title compound.

¹H NMR (300 MHz, CDCl₃) δ7.6 (bs, 4H), 7.5 (d, J=7 Hz, 2H), 6.95 (d, J=7 Hz, 2H), 4.05 (m, 2H), 3.8 (m, 2H), 2.2 (m, 2H); MS (EI) 310 (M+H)⁺.

EXAMPLE 10E

4-{[4'-(3-chloropropoxy)[1,1'-biphenyl]-4-yl]carbonyl}morpholine

The product from Example 10D (185 mg, 0.6 mmol), morpholine (0.058 ml, 0.65 mmol) and diisopropylethylamine (100 μl, 0.6 mmol) in 2 mL of dichloromethane were stirred at 20° C. for 18 hours. The mixture was evaporated

EXAMPLE 10F

4-[(4'-{3-[(2R,5R)-2,5-dimethylpyrrolidinyl] propoxy}[1,1'-biphenyl]-4-yl)carbonyl]morpholine The product from Example 10E (30 mg, 0.084 mmol), (2R,5R)-2,5-dimethylpyrrolidine hydrochloride (50 mg, 0.5 mmol) (purchased from Toronto Research Chemicals, TRC), 75 mg of potassium carbonate and 75 mg of potassium iodide in 5 mL of 2-butanone were heated at 80° C. for 72 hours. The mixture was allowed to cool to ambient temperature, filtered and the filtrate was evaporated under reduced pressure. The residue was purified by HPLC chromatography (C18 reverse phase Water's 25 mm module prep column, 10 to 95% acetonitrile/0.1% TFA in water, 10 minute linear gradient, flow rate 40 mL/minute) to provide the title compound (70% yield).

$^1$H NMR (300 MHz, CDCl$_3$) δ0.99 (d, 6H, J=6.1 Hz), 1.38 (m, 2H), 1.66 (m, 1H), 1.88–2.10 (m, 4H), 2.57 (m, 1H), 2.78 (m, 1H), 3.06 (m, 2H), 3.43–3.81 (m, 8H), 4.08 (m, 2H), 6.99 (m, 2H), 7.48 (m, 4H), 7.59 (m, 2H); MS (APCI) m/z 423 (M+H)$^+$.

EXAMPLE 11

N-methyl-N-[(1R)-1-phenylethyl]-N-(3-{[4'-(1'-pyrrolidinylcarbonyl)[1,1'-biphenyl]-4-yl]oxy}propyl)amine

EXAMPLE 11A

1{[4'-(3-chloropropoxy)[1,1'-biphenyl]-4-yl]carbonyl}pyrrolidine

The product from Example 10D and pyrrolidine were processed as described in Example 10E to provide the title compound.

EXAMPLE 11B

N-methyl-N-[(1R)-1-phenylethyl]-N-(3-{[4'-(1-pyrrolidinylcarbonyl)[1,1'-biphenyl]-4-yl]oxy}propyl)amine The product from Example 11A and N-methyl-N-[(1R)-1-phenylethyl]amine were processed as described in Example 10F to provide the title compound.

$^1$H NMR (500 MHz, CDCl$_3$) δ1.81 (d, 3H, J=6.8 Hz), 1.89 (m, 6H), 1.98 (m, 3H), 2.15–2.45 (m, 2H), 2.68 (s, 3H), 2.88 (m, 1H), 3.00 (m, 1H), 3.41 (m, 1H), 3.50 (m, 2H), 3.67 (m, 2H), 4.06 (m, 2H), 4.48 (m, 1H), 6.91 (m, 2H), 7.45 (m, 5H), 7.52 (m, 2H), 7.57 (m, 4H); MS (APCI) m/z 443 (M+H)$^+$.

EXAMPLE 12

N-[(3R)-1-benzylpyrrolidinyl]-N-methyl-N-(3-{[4'-(1-pyrrolidinylcarbonyl)[1,1'-biphenyl]-4-yl]oxy}propyl)amine The product from Example 11A and N-[(3R)-1-benzylpyrrolidinyl]-N-methylamine were processed as described in Example 10F to provide the title compound.

$^1$H NMR (500 MHz, CDCl$_3$) δ1.89 (m, 2H), 1.98 (m, 2H), 2.26 (m, 2H), 2.56 (m, 2H), 2.85 (s, 3H), 3.27 (m, 2H), 3.41 (m, 1H), 3.52 (m, 3H), 3.67 (m, 2H), 3.84 (m, 2H), 4.10 (m, 2H), 4.28 (s, 2H), 6.92 (m, 2H), 7.44 (m, 5H), 7.53 (m, 2H), 7.57 (m, 4H); MS (APCI) m/z 498 (M+H)$^+$.

EXAMPLE 13

[(2R)-1-(3-{[4'-(1-pyrrolidinylcarbonyl)[1,1'-biphenyl]-4-yl]oxy}propyl)pyrrolidinyl]methanol The product from Example 11A and (2R)-pyrrolidinylmethanol were processed as described in Example 10F to provide the title compound.

$^1$H NMR (500 MHz, CDCl$_3$) δ1.94 (m, 5H), 2.04–2.42 (m, 1H), 2.99 (m, 1H), 3.24 (m, 1H), 3.52 (m, 3H), 3.67 (m, 3H), 3.89 (m, 3H), 4.07 (m, 1H), 4.13 (m, 1H), 6.94 (m, 2H), 7.53 (m, 2H), 7.57 (m, 4H); MS (APCI) m/z 409 (M+H)$^+$.

EXAMPLE 14

[(2S)-1-(3-{[4'-(1-pyrrolidinylcarbonyl)[1,1'-biphenyl]-4-yl]oxy}propyl)pyrrolidinyl]methanol The product from Example 11A and (2S)-pyrrolidinylmethanol were processed as described in Example 10F to provide the title compound.

$^1$H NMR (500 MHz, CDCl$_3$) δ1.94 (m, 5H), 2.04–2.42 (m, 10H), 2.99 (m, 1H), 3.24 (m, 1H), 3.51 (m, 3H), 3.67 (m, 3H), 3.89 (m, 3H), 4.07 (m, 1H), 4.13 (m, 1H), 6.95 (m, 2H), 7.53 (m, 2H), 7.57 (m, 4H); MS (APCI) m/z 409 (M+H)$^+$.

EXAMPLE 15

(2R,6S)-2,6-dimethyl-1-(3-{[4'-(1-pyrrolidinylcarbonyl)[1,1'-biphenyl]-4-yl]oxy}propyl)piperidine The product from Example 11A and (2R,6S)-2,6-dimethylpiperidine were processed as described in Example 10F to provide the title compound.

$^1$H NMR (500 MHz, CDCl$_3$) δ1.52 (d, 3H, J=6.2 Hz), 1.71 (m, 1H), 1.86 (m, 4H), 1.98 (m, 2H), 2.12 (m, 3H), 2.25 (m, 5H), 2.38 (m, 1H), 3.05 (m, 2H), 3.50 (m, 2H), 3.57 (m, 1H), 3.68 (m, 2H), 3.76 (m, 1H), 4.11 (m, 2H), 6.94 (m, 2H), 7.53 (m, 2H), 7.59 (m, 4H); MS (APCI) m/z 421 (M+H)$^+$.

EXAMPLE 16

(3R)-1-(3-{[4'-(1-pyrrolidinylcarbonyl)[1,1'-biphenyl]-4-yl]oxy}propyl)-3-piperidinol The product from Example 11A and (3R)-3-piperidinol were processed as described in Example 10F to provide the title compound.

$^1$H NMR (500 MHz, CDCl$_3$) δ1.59 (m, 1H), 1.77 (m, 1H), 1.88 (m, 2H), 1.97 (m, 3H), 2.06 (m, 1H), 2.16 (m, 1H), 2.30 (m, 5H), 2.47 (m, 2H), 2.69 (m, 1H), 2.83 (m, 1H), 3.24 (m, 2H), 3.49 (m, 2H), 3.67 (m, 3H), 3.80 (m, 1H), 4.06 (m, 2H), 4.25 (m, 1H), 6.93 (m, 2H), 7.52 (m, 2H), 7.57 (m, 4H). MS (APCI) m/z 409 (M+H)$^+$.

Determination of Biological Activity

Histamine-3Receptor Binding

To determine the effectiveness of representative compounds of this invention as histamine-3 receptor ligands (H$_3$ receptor ligands), the following tests were conducted according to methods previously described (European Journal of Pharmacology, 188:219–227 (1990); Journal of Pharmacology and Experimental Therapeutics, 275: 598–604

(1995); Journal of Pharmacology and Experimental Therapeutics, 276:1009–1015 (1996); and Biochemical Pharmacology, 22: 3099–3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL of 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid $N_2$ and stored at −70° C. until used in assays. Rat cortical membranes (12 mg wet weight/tube) were incubated with ($^3$H)-N-α-methylhistamine (~0.6 nM) with or without $H_3$ receptor antagonists in a total incubation volume of 0.5 mL of 50 mM Tris-HCl/5 mM EDTA (pH 7.7). Test compounds were dissolved in DMSO to provide a 20 mM solution, serially diluted and then added to the incubation mixtures prior to initiating the incubation assay by addition of the membranes. Thioperamide (3 μM) was used to determine nonspecific binding. Binding incubations were conducted for 30 minutes at 25° C. and terminated by addition of 2 mL of ice cold 50 mM Tris-HCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and Ki values were determined using the Cheng-Prusoff equation.

TABLE 1

| Example Number | Ki (nM) |
|---|---|
| 1 | 2.84 |
| 2 | 2.04 |
| 3 | 1.00 |
| 4 | 507 |
| 5 | 13.8 |
| 6 | 4.20 |
| 7 | 3.66 |
| 8 | 114 |
| 9 | 2.63 |
| 10 | 1.66 |
| 11 | 363 |
| 12 | 384 |
| 13 | 80.0 |
| 14 | 6.07 |
| 15 | 7.18 |
| 16 | 71.5 |

As shown by the data in Table 1, the compounds of the present invention bind to the histamine-3 receptor and therefore may have utility in the treatment of diseases or conditions ameliorated with histamine-3 receptor ligands.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974Recommendations for Section E, Fundamental Stereochemistry, Pure Appl. Chem., 1976, 45: 13–30. However, the present invention does contemplate various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula (I) prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N. Y., (1976), p 33 et seq.

The terms "pharmaceutically acceptable salts, esters and amides," as used herein, refer to carboxylate salts, amino acid addition salts, zwitterions, esters and amides of compounds of formula (I) which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66:1 et seq. The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the present invention include phosphate, tris and acetate.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

The present invention contemplates pharmaceutically active compounds either chemically synthesized or formed by in vivo biotransformation to compounds of formula (I).

The compounds of the present invention, including but not limited to those specified in the examples, possess an affinity for the histamine-3 receptor. As histamine-3 receptor ligands, the compounds of the present invention may be useful for the treatment and prevention of diseases or conditions such as acute myocardial infarction, Alzheimer's disease, attention-deficit hyperactivity disorder, Parkinson's disease, epilepsy, schizophrenia, depression, cutaneous carcinoma, medullary thyroid carcinoma, melanoma, asthma, narcolepsy, Meniere's disease, gastrointestinal disorders, inflammation, migraine, motion sickness, obesity, pain, seizures, and septic shock.

The ability of the compounds of the present invention, including but not limited to those specified in the examples, to treat septic shock and cardiovascular disorders, in particular, acute myocardial infarction may be demonstrated by Imamura et al., Circ.Res., (1996) 78, 475–481; Imamura et. al., Circ.Res., (1996) 78, 863–869;R. Levi and N.C.E. Smith, "Histamine $H_3$-receptors: A new frontier in myocardial ischemia", J. Pharm. Exp. Ther., 292: 825–830, (2000); and Hatta, E., K Yasuda and R. Levi, "Activation of histamine $H_3$ receptors inhibits carrier-mediated norepinephrine release in a human model of protracted myocradial ischemia", J. Pharm. Exp. Ther., 283: 494–500, (1997).

The ability of the compounds of the present invention, including but not limited to those specified in the examples, to treat sleep disorders, in particular, narcolepsy may be demonstrated by Lin et al., Brain Res. (1990) 523, 325–330; Monti et al., Neuropsychopharmacology (1996) 15, 31–35; Sakai, et al., Life Sci. (1991) 48, 2397–2404; Mazurkiewicz-Kwilecki and Nsonwah, Can. J. Physiol. Pharmacol. (1989) 67, 75–78; Panula, P. et al., Neuroscience (1998) 44, 465–481); Wada et al., Trends in Neuroscience (1991) 14, 415); and Monti et al., Eur. J. Pharmacol. (1991) 205, 283.

The ability of the compounds of the present invention, including but not limited to those specified in the examples, to treat cognition and memory process disorders may be demonstrated by Mazurkiewicz-Kwilecki and Nsonwah, Can. J. Physiol. Pharmacol. (1989) 67, 75–78; Panula, P. et al., Neuroscience (1998) 44, 465–481; Haas et al., Behav. Brain Res. (1995) 66, 41–44; De Almeida and Izquierdo, Arch. Int. Pharmacodyn. (1986) 283, 193–198; Kamei et al., Psychopharmacology (1990) 102, 312–318; and Kamei and Sakata, Jpn. J. Pharmacol. (1991) 57, 437–482); Schwartz et al., Psychopharmacology; The fourth Generation of Progress. Bloom and Kupfer (eds). Raven Press, New York, (1995) 397; and Wada et al., Trends in Neurosci., (1991) 14, 415.

The ability of the compounds of the present invention, including but not limited to those specified in the examples, to treat attention-deficit hyperactivity disorder (ADHD) may be demonstrated by Shaywitz et al., Psychopharmacology (1984) 82, 73–77; Dumery and Blozovski, Exp. Brain Res. (1987) 67, 61–69; Tedford et al., J. Pharmacol. Exp. Ther. (1995) 275, 598–604; and Tedford et al., Soc. Neurosci. Abstr. (1996) 22, 22.

The ability of the compounds of the present invention, including but not limited to those specified in the examples, to treat seizures, in particular, epilepsy may be demonstrated by Yokoyama et al., Eur. J. Pharmacol. (1993) 234, 129; Yokoyama and Iinuma, CNS Drugs (1996) 5, 321; Onodera et al., Prog. Neurobiol. (1994) 42, 685; R. Leurs, R. C. Vollinga and H. Timmerman, "The medicinal chemistry and therapeutic potentials of ligand of the histamine $H_3$ receptor", Progress in Drug Research 45: 170–165, (1995); Leurs and Timmerman, Prog. Drug Res. (1992) 39, 127; The Histamine $H_3$ Receptor, Leurs and Timmerman (eds), Elsevier Science, Amsterdam, The Netherlands (1998); H. Yokoyama and K. Iinuma, "Histamine and Seizures: Implications for the treatment of epilepsy", CNS Drugs, 5(5); 321–330, (1995); and K. Hurukami, H. Yokoyama, K. Onodera, K. Iinuma and T. Watanabe, AQ-0145, "A newly developed histamine $H_3$ antagonist, decreased seizure susceptibility of electrically induced convulsions in mice", Meth. Find. Exp. Clin. Pharmacol., 17(C): 70–73, (1995).

The ability of the compounds of the present invention, including but not limited to those specified in the examples, to treat motion sickness, Alzheimer's disease, and Parkinson's disease may be demonstrated by Onodera et al., Prog. Neurobiol. (1994) 42, 685; Leurs and Timmerman, Prog. Drug Res. (1992) 39, 127; and The Histamine $H_3$ Receptor, Leurs and Timmerman (eds), Elsevier Science, Amsterdam, The Netherlands (1998).

The ability of the compounds of the present invention, including but not limited to those specified in the examples, to treat narcolepsy, schizophrenia, depression, and dementia may be demonstrated by R. Leurs, R. C. Vollinga and H. Timmerman, "The medicinal chemistry and therapeutic potentials of ligand of the histamine $H_3$ receptor", Progress in Drug Research 45: 170–165, (1995); and The Histamine $H_3$ Receptor, Leurs and Timmerman (eds), Elsevier Science, Amsterdam, The Netherlands (1998).

The ability of the compounds of the present invention, including but not limited to those specified in the examples, to treat obesity may be demonstrated by Leurs et al., Trends in Pharm. Sci. (1998) 19, 177–183.

The ability of the compounds of the present invention, including but not limited to those specified in the examples, to treat inflammation and pain may be demonstrated by Phillips et al., Annual Reports in Medicinal Chemistry (1998) 33, 31–40.

The ability of the compounds of the present invention, including but not limited to those specified in the examples, to treat migraine may be demonstrated by R. Leurs, R. C. Vollinga and H. Timmerman, "The medicinal chemistry and therapeutic potentials of ligand of the histamine $H_3$ receptor", Progress in Drug Research 45: 170–165, (1995); and Matsubara et al., Eur. J. Pharmacol. (1992) 224, 145; and Rouleau et al., J. Pharmacol. Exp. Ther. (1997) 281, 1085.

The ability of the compounds of the present invention, including but not limited to those specified in the examples, to treat cancer, in particular, melanoma, cutaneous carcinoma and medullary thyroid carcinoma may be demonstrated by Polish Med. Sci. Mon., (1998) vol. 4, issue 5, 747; Adam Szelag, "Role of histamine $H_3$-receptors in the proliferation of neoplastic cells in vitro", Med. Sci. Monit., 4(5): 747–755, (1998); and Fitzsimons, C., H. Duran, F. Labombarda, B. Molinari and E. Rivera, "Histamine receptors signalling in epidermal tumor cell lines with H-ras gene alterations", Inflammation Res., 47 (Suppl 1): S50–S51, (1998).

The ability of the compounds of the present invention, including but not limited to those specified in the examples, to treat vestibular dysfunctions, in particular, Meniere's disease may be demonstrated by R. Leurs, R. C. Vollinga and H. Timmerman, "The medicinal chemistry and therapeutic potentials of ligand of the histamine $H_3$ receptor", Progress in Drug Research 45: 170–165, (1995).

The ability of the compounds of the present invention, including but not limited to those specified in the examples, to treat asthma may be demonstrated by Delaunois A., Gustin P., Garbarg M., and Ansay M., "Modulation of acetylcholine, capsaicin and substance P effects by histamine $H_3$ receptors in isolated perfused rabbit lungs", European Journal of Pharmacology 277(2–3):243–50, (1995); and Dimitriadou, et al., "Functional relationship between mast cells and C-sensitive nerve fibres evidenced by histamine $H_3$-receptor modulation in rat lung and spleen", Clinical Science. 87(2):151–63, (1994).

Aqueous liquid compositions of the present invention are particularly useful for the treatment and prevention of asthma, epilepsy, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of the present invention administered to a human or lower animal may range from about 0.003 to about 30 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

What is claimed is:

1. A compound of formula (I)

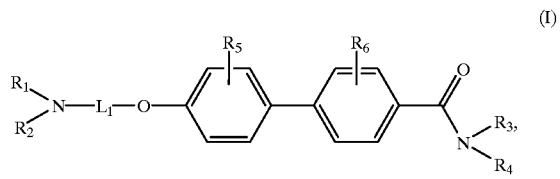

or a pharmaceutically acceptable salt thereof, wherein
$L_1$ is alkylene;
$R_1$ and $R_2$ are each independently selected from the group consisting of hydrogen, alkyl, aryl, arylalkyl, cycloalkyl, cycloalkylalkyl, heterocycle and heterocyclealkyl; or
$R_1$ and $R_2$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl;
$R_3$ and $R_4$ are each independently selected from the group consisting of hydrogen, alkyl, aryl, arylalkyl, cycloalkyl, cycloalkylalkyl, heterocycle and heterocyclealkyl; or
$R_3$ and $R_4$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; and
$R_5$ and $R_6$ are each independently selected from the group consisting of hydrogen, alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$)sulfonyl;

provided that when $R_1$ and $R_2$ together form pyrrolidinyl and wherein said pyrrolidinyl is substituted with 1 substituent then said substituent is other than alkoxy, hydroxy or —$NR_AR_B$.

2. A compound according to claim 1 wherein $L_1$ is —$CH_2CH_2CH_2$—;

$R_1$ and $R_2$ are each independently selected from the group consisting of hydrogen, alkyl, arylalkyl and heterocycle; or $R_1$ and $R_2$ taken together with the nitrogen atom to which they are attached, together form a heterocycle selected from the group consisting of morpholinyl, piperidinyl and pyrrolidinyl; and $R_3$ and $R_4$ are each independently selected from the group consisting of hydrogen and alkyl; or $R_3$ and $R_4$ taken together with the nitrogen atom to which they are attached, together form a heterocycle selected from the group consisting of morpholinyl, piperidinyl and pyrrolidinyl.

3. A compound according to claim 1 wherein $L_1$ is selected from the group consisting of —$CH_2CH_2$— and —$CH_2CH_2CH_2$—;

$R_1$ and $R_2$ are each independently selected from the group consisting of hydrogen, alkyl, aryl, arylalkyl, cycloalkyl, cycloalkylalkyl, heterocycle and heterocyclealkyl; and $R_3$ and $R_4$ are each independently selected from the group consisting of hydrogen, alkyl, aryl, arylalkyl, cycloalkyl, cycloalkylalkyl, heterocycle and heterocyclealkyl.

4. A compound according to claim 1 wherein $L_1$ is —$CH_2CH_2CH_2$—;

$R_1$ and $R_2$ are each independently selected from the group consisting of hydrogen, alkyl, arylalkyl and heterocycle; and $R_3$ and $R_4$ are each independently selected from the group consisting of hydrogen and alkyl.

5. A compound according to claim 1 wherein $L_1$ is —$CH_2CH_2CH_2$—;

$R_1$ and $R_2$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; and $R_3$ and $R_4$ are each independently selected from the group consisting of hydrogen, alkyl, aryl, arylalkyl, cycloalkyl, cycloalkylalkyl, heterocycle and heterocyclealkyl.

6. A compound according to claim 1 wherein $L_1$ is —$CH_2CH_2CH_2$—;

$R_1$ and $R_2$ taken together with the nitrogen atom to which they are attached, together form a heterocycle selected from the group consisting of morpholinyl, piperidinyl and pyrrolidinyl; and $R_3$ and $R_4$ are each independently selected from the group consisting of hydrogen and alkyl.

7. A compound according to claim 6 selected from the group consisting of

4'-{3-[(2R,5R)-2,5-dimethylpyrrolidinyl]propoxy}-N-isopropyl[1,1'-biphenyl]-4-carboxamide; and 4'-{3-[(2R,5R)-2,5-dimethylpyrrolidinyl]propoxy}-N,N-diethyl[1,1'-biphenyl]-4-carboxamide.

8. A compound according to claim 1 wherein $L_1$ is selected from the group consisting of —$CH_2CH_2$— and —$CH_2CH_2CH_2$—;

$R_1$ and $R_2$ are each independently selected from the group consisting of hydrogen, alkyl, aryl, arylalkyl, cycloalkyl, cycloalkylalkyl, heterocycle and heterocyclealkyl; and $R_3$ and $R_4$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl.

9. A compound according to claim 1 wherein $L_1$ is —$CH_2CH_2CH_2$—;

$R_1$ and $R_2$ are each independently selected from the group consisting of hydrogen, alkyl, arylalkyl and heterocycle; and $R_3$ and $R_4$ taken together with the nitrogen atom to which they are attached, together form a heterocycle selected from the group consisting of morpholinyl, piperidinyl and pyrrolidinyl.

10. A compound according to claim 9 selected from the group consisting of

3-[(4'-{[(2R,5R)-2,5-dimethylpyrrolidinyl]carbonyl}[1,1'-biphenyl]-4-yl)oxy]N-isopropyl-1-propanamine;

3-[(4'-{[(2R,5R)-2,5-dimethylpyrrolidinyl]carbonyl}[1,1'-biphenyl]-4-yl)oxy]-N,N-diethyl-1-propanamine;

N-methyl-N-[(1R)-1-phenylethyl]-N-(3{-[4'-(1-pyrrolidinylcarbonyl)[1,1'-biphenyl]-4-yl]oxy}propyl)amine; and N-[(3R)-1-benzylpyrrolidinyl]-N-methyl-N-(3-{[4'-(1-pyrrolidinylcarbonyl)[1,1'-biphenyl]-4-yl]oxy}propyl)amine.

11. A compound according to claim 1 wherein $L_1$ is selected from the group consisting of —$CH_2CH_2$— and —$CH_2CH_2CH_2$—;

$R_1$ and $R_2$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl; and $R_3$ and $R_4$ taken together with the nitrogen atom to which they are attached, together form a heterocycle selected from the group consisting of azepanyl, azetidinyl, morpholinyl, piperazinyl, piperidinyl, pyrrolidinyl, 2,5-dihydro-1H-pyrrolyl, pyrrolyl, thiomorpholinyl and 1,1-dioxidothiomorpholinyl.

12. A compound according to claim 1 wherein $L_1$ is —$CH_2CH_2CH_2$—;

$R_1$ and $R_2$ taken together with the nitrogen atom to which they are attached, together form a heterocycle selected from the group consisting of morpholinyl, piperidinyl and pyrrolidinyl; and $R_3$ and $R_4$ taken together with the nitrogen atom to which they are attached, together form a heterocycle selected from the group consisting of morpholinyl, piperidinyl and pyrrolidinyl.

13. A compound according to claim 12 selected from the group consisting of (2R,5R)-2,5-dimethyl-1-[3-({4'-[(2-methyl-1-pyrrolidinyl)carbonyl][1,1'-biphenyl]-4-yl}oxy)propyl]pyrrolidine;

(2R,5R)-1-[(4'-{3-[(2R,5R)-2,5-dimethylpyrrolidinyl]propoxy}[1,1'-biphenyl]-4-yl)carbonyl]-2,5-dimethylpyrrolidine;

1-{3-[(4'-{[(2R,5R)-2,5-dimethylpyrrolidinyl]carbonyl}[1,1'-biphenyl]-4-yl)oxy]propyl}-4-methylpiperidine;

4-{3-[(4'-{[(2R,5R)-2,5-dimethylpyrrolidinyl]carbonyl}[1,1'-biphenyl]-4-yl)oxy]propyl}morpholine;

1-[(4'-{3-[(2R,5R)-2,5-dimethylpyrrolidinyl]propoxy}[1,1'-biphenyl]-4-yl)carbonyl]-4-methylpiperidine;

[(2R)-1-(3-{[4'-(1-pyrrolidinylcarbonyl)[1,1'-biphenyl]-4-yl]oxy}propyl)pyrrolidinyl]methanol;

[(2S)-1-(3-{[4'-(1-pyrrolidinylcarbonyl)[1,1'-biphenyl]-4-yl]oxy}propyl)pyrrolidinyl]methanol;

(2R,6S)-2,6-dimethyl-1-(3-{[4'-(1-pyrrolidinylcarbonyl)[1,1'-biphenyl]-4-yl]oxy}propyl)piperidine; and (3R)-1-(3-{[4'-(1-pyrrolidinylcarbonyl)[1,1'-biphenyl]-4-yl]oxy}propyl)-3-piperidinol.

14. A compound according to claim 12 that is 4-[(4'-{3-[(2R,5R)-2,5-dimethylpyrrolidinyl]propoxy}[1,1'-biphenyl]-4-yl)carbonyl]morpholine.

15. A pharmaceutical composition comprising a therapeutically effective amount of a compound of claim 1 in combination with a pharmaceutically acceptable carrier.

16. A method for modulating the effects of the histamine-3 receptor in a mammal comprising administering a therapeutically effective amount of a compound of claim 1.

17. A method of treating a disorder wherein the disorder is ameliorated by modulating the histamine-3 receptor in a mammal in need of such treatment comprising administering a therapeutically effective amount of a compound of claim 1.

18. The method of claim 17 wherein the disorder is selected from the group consisting of acute myocardial infarction, asthma, cutaneous carcinoma, depression, inflammation, medullary thyroid carcinoma, melanoma, Meniere's disease, migraine, motion sickness, obesity, pain, Parkinson's disease, seizures, and septic shock.

19. The method of claim 17 wherein the disorder is Alzheimer's disease.

20. The method of claim 17 where in the disorder is attention-deficit hyperactivity disorder.

21. The method of claim 17 wherein the disorder is epilepsy.

22. The method of claim 17 wherein the disorder is schizophrenia.

* * * * *

UNITED STATES PATENT AND TRADEMARK OFFICE
CERTIFICATE OF CORRECTION

PATENT NO.   : 6,316,475 B1
DATED        : November 13, 2001
INVENTOR(S)  : Bennani, Youssef L., et al.

It is certified that error appears in the above-identified patent and that said Letters Patent is hereby corrected as shown below:

Title page,
Item [57], ABSTRACT,
Remove the comma from R3 in the formula

Column 32,
Line 1, replace "modulating" with -- ameliorating --
Line 5, replace "ameliorated by modulating" with -- treated by ameliorating --

Signed and Sealed this

Eighth Day of October, 2002

*Attest:*

JAMES E. ROGAN
*Director of the United States Patent and Trademark Office*

*Attesting Officer*